United States Patent

Tsutsumi et al.

Patent Number: 5,618,801
Date of Patent: Apr. 8, 1997

[54] COMPOSITION FOR PREVENTING AND TREATING CATARACT

[75] Inventors: Kazuhiko Tsutsumi, Tokushima; Yasuhide Inoue, Naruto; Chieko Yoshida, Naruto; Yoshihiko Tsuda, Naruto, all of Japan

[73] Assignee: Otsuka Pharmaceutical Factory, Inc., Tokushima-ken, Japan

[21] Appl. No.: 178,829

[22] Filed: Jan. 7, 1994

[51] Int. Cl.$^6$ .......................... A61K 31/66; A61K 31/195
[52] U.S. Cl. .......................... 514/75; 514/563; 514/912
[58] Field of Search .............................. 514/75, 563, 912

[56] References Cited

FOREIGN PATENT DOCUMENTS 5953   1/1993   Japan .

OTHER PUBLICATIONS

Chemical Abstract 114: 163766 (1990). Tsutsumi et al.

*Primary Examiner*—Zohreh Fay
*Attorney, Agent, or Firm*—Sughrue, Mion, Zinn, Macpeak & Seas

[57] ABSTRACT

The present invention provides an agent for preventing and treating cataract comprising, as an active ingredient, a carboxylic acid amide derivative represented by the general formula:

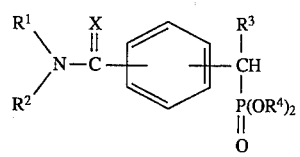

wherein $R^1$, $R^2$, $R^3$, $R^4$ and X are as defined above.

The present invention has a marked preventive and therapeutic effect on the cataract belonging to various classifications and particularly on the diabetic cataract.

4 Claims, 1 Drawing Sheet

COMPOSITION FOR PREVENTING AND TREATING CATARACT

FIELD OF THE INVENTION

The present invention relates to an agent for preventing and treating cataract, more particularly, to an agent for preventing and treating cataract which contains a specified carboxylic acid amide derivative as an active ingredient.

PRIOR ART AND THE PROBLEM TO BE SOLVED

The present invention relates to an agent for preventing and treating cataract which contains, as an active ingredient, a carboxylic acid amide derivative represented by the following general formula (1):

$$\begin{matrix} R^1 & X \\ \diagdown & \| \\ & N-C \end{matrix} \!\!-\!\!\left[\text{phenylene}\right]\!\!-\!\! \begin{matrix} R^3 \\ | \\ CH \\ | \\ P(OR^4)_2 \\ \| \\ O \end{matrix} \quad (1)$$

wherein:

$R^1$ and $R^2$ taken individually each represents a hydrogen atom, an alkyl group, a cycloalkyl group, a diphenyl-lower alkyl group or a group of the formula:

[structure with $R^5$, $R^6$, $R^7$ substituents on a phenyl ring and $(A)_l$—]

in which $R^5$, $R^6$ and $R^7$ each represents a hydrogen atom, a halogen atom, a nitro group, a lower alkoxy group, a lower alkoxycarbonyl group, a lower alkyl group, a halogen-substituted lower alkyl group, a cyano group, a carboxyl group or a hydroxyl group;

A represents a lower alkylene group; and l represents 0 or 1; or $R^1$ and $R^2$ may form a heterocyclic group by combining with the adjacent nitrogen atom being bonded thereto, together with or without other nitrogen atom or oxygen atom, said heterocyclic group being unsubstituted or substituted by a lower alkyl group, a phenyl-lower alkyl group or a phenyl group unsubstituted or substituted with lower alkyl group(s), lower alkoxy group(s), halogen atom(s) or halogen-substituted lower alkyl group(s);

$R^3$ represents a hydrogen atom, an alkyl group or a phenyl-lower alkyl group;

$R^4$ represents a lower alkyl group or a phenyl group; and

X represents an oxygen atom or a sulfur atom.

The carboxylic acid amide derivatives represented by the above-mentioned general formula (1) are known compounds which have already been developed by the present inventors as compounds effectively applicable to pharmaceutical uses such as the use as anti-inflammatory agent or the like (Japanese Patent Kokai No. 61-151199), and afterwards as active ingredient of an agent for treating hyperlipidemia (Japanese Patent Kokai No. 63-264421). These derivatives can be obtained according to the method mentioned in these patent gazettes.

Further, the carboxylic acid amide derivatives represented by the general formula (2) have also been developed previously (Japanese Patent Application No. 2-116525) by the present inventors as active ingredient of an agent for treating hyperlipidemia, and their production is as mentioned later in this specification.

However, none of the patent gazettes mentioned above refer to the effectiveness of these carboxylic acid amide derivatives for prevention and treatment of cataract, at all. Further, no report has ever pointed out the usefulness of these carboxylic acid amide derivatives in any pharmaceutical uses, except for the above-mentioned patent gazettes. Needless to say, application of these derivatives to the ophthalmic field has never been proposed.

Cataract is a disease caused by opacity of the crystalline lens of the eye. It is further classified into the following diseases:

1) senile cataract,
2) traumatic cataract caused by trauma such as contusion, punctured wound, incised wound, etc.,
3) complicated cataract following non-traumatic diseases of the eye-ball,
4) diabetic cataract observed in patient of diabetes mellitus, and
5) congenital cataract.

Today, however, the cause of the disease is not yet fully elucidated.

As agent for treating cataract, there are known today a variety of medicinal materials such as Succus Cineraria Maritime ophthalmic solution of which main component is constituted of two medical herbs, Catalin ophthalmic solution and Phacolysin ophthalmic solution acting so as to prevent the lens protein denaturation effect, Tathion, Glutation and the like controlling the oxidation-reduction system, and salivary gland hormone preparations for oral administration use such as Parotin, Tiopronin and the like. All these agents available today, however, have some problems as an agent for treating cataract, and solution of such problems by development of a new agent for treating cataract capable of replacing the existing agents is awaited.

MEANS FOR SOLVING THE PROBLEMS

In view of the above-mentioned circumstances, the present inventors conducted extensive studies to find that the specified carboxylic acid amide derivatives represented by the above general formula (1) and the following general formula (2) are effectively usable for prevention and treatment of cataract. Based on the finding, the present invention provides herein a novel agent for preventing and treating cataract.

Of the compounds of general formula (1) which can be used as an active ingredient of the agent for preventing and treating cataract of the invention, preferred are those represented by the following general formula (2):

$$\begin{matrix} R^{5'} & & H & O \\ & & | & \| \\ R^{6'} & & N-C \end{matrix} \!\!-\!\!\left[\text{phenylene}\right]\!\!-\!\! \begin{matrix} CH_2 \\ | \\ P(OR^{4'})_2 \\ \| \\ O \end{matrix} \quad (2)$$

wherein $R^{4'}$ represents a lower alkyl group, $R^{5'}$ represents a cyano group, $R^{6'}$ represents a halogen atom, and $R^{7'}$ represents a hydrogen atom or a halogen atom; among which 4-diethoxyphosphinoylmethyl-N-(4-bromo-2-cyanophenyl)benzamide is the most successfully usable.

The present invention has been accomplished on the basis of a discovery that the derivatives represented by the general formula (1) and general formula (2) have preventive and therapeutic effects on cataract which is by no means related to the hitherto known pharmaceutical uses of these derivatives. The preventive and therapeutic effects of these derivatives are noticeable on all the cataracts belonging to any classifications mentioned above, and particularly markedly exhibited on the diabetic cataract.

DETAILED EXPLANATION OF THE INVENTION

An indispensably necessary condition of the present invention is that the agent of the invention for preventing and treating cataract contains at least one member selected from the compounds inclusively represented by the general formulas (1) and (2) as an active ingredient. Usually, said compound is formed into a preparation of pharmaceutical composition depending on the desired method of administration together with a conventional pharmaceutically acceptable non-toxic carrier, and applied to patients having cataract as an agent for preventing and treating cataract, or used as an agent for preventing cataract. Examples of the pharmaceutically acceptable carrier usable herein include a variety of ones used depending on the desired form of preparation, such as diluent or solvent, filler, excipient, binder, suspension stabilizer, disintegrating agent, surface active agent, lubricant, vehicle, wetting agent and the like. Into the preparation, usual dissolving agents, buffering agents, preservatives, coloring materials, perfumes, seasoning agents and the like may be incorporated appropriately, if necessary.

In the therapeutic agent of the invention, the form of preparation is not restricted, and it may be selected appropriately. For example, a variety of forms including oral preparations such as tablets, capsules, granules, pills, syrups, liquors, emulsions, suspensions and the like, and non-oral preparations including injection preparations (such as subcutaneous injection, intravenous injection, intramuscular injection, intraperitoneal injection and the like), ophthalmic solutions, etc. may be adopted appropriately.

The agent of the invention is made into the above-mentioned various preparation forms according to the usual methods. Thus, oral preparations such as tablet, capsule, granule, pill and the like can be produced by using an excipient such as white sugar, lactose, glucose, starch, mannit and the like; a binder such as syrup, gum arabic, sorbit, tragacanth gum, methyl cellulose, polyvinylpyrrolidone and the like; disintegrating agents such as starch, carboxymethyl cellulose or calcium salt thereof, microcrystalline cellulose, polyethylene glycol and the like; a lubricant such as talc, magnesium stearate, calcium stearate, silica and the like; a wetting agent such as sodium laurate, glycerol and the like; etc. Injection preparations, solutions, emulsions, suspensions, syrups, etc. are prepared in the usual manner by using a solvent for dissolving the active ingredients, such as ethyl alcohol, isopropyl alcohol, propylene glycol, 1,3-butylene glycol, polyethylene glycol, sesame oil and the like, a surface active agent such as sorbitan fatty acid ester, polyoxyethylene sorbitan fatty acid ester, polyoxyethylene fatty acid ester, hydrogenated castor oil-polyoxyethylene ether, lecithin and the like, a suspension stabilizer including cellulose derivatives such as sodium carboxymethyl cellulose, methyl cellulose and the like and natural gums such as tragacanth gum, arabic gum and the like, a preservative such as p-oxybenzoic ester, benzalkonium chloride, sorbic acid salt and the like, etc. appropriately. An ophthalmic solution is prepared in the usual manner by using sterilized distilled water as a base and appropriately using a buffering agent such as sodium dihydrogen phosphate, sodium monohydrogen phosphate and the like, an isotonic agent such as sodium chloride and the like, an antiseptic such as Benzethonium Chloride, Chlorobutanol and the like, etc.

The dosage of the agent for preventing and treating cataract of the present invention may be arbitrarily selected depending on the form of preparation, the route of administration, the age, body weight and sensibility of patient, the degree of the symptoms, etc., and is not particularly restricted. Usually, as expressed in terms of the quantity of active ingredient contained in a preparation, about 0.05 to about 80 mg, preferably about 0.1 to about 50 mg, may be administered per 1 kg of body weight per day in the case of oral preparations, though the dosage may be appropriately increased or decreased if necessary. In the case of ophthalmic solution, the dosage may be selected from such a range as to give an effective dosage per one administration of about 0.3 to about 2 µg.

Next, the method for producing the compound of general formula (2) used as active ingredient of the invention will be mentioned below in detail. The compound can be produced according to the method represented by the following Reaction Scheme-1.

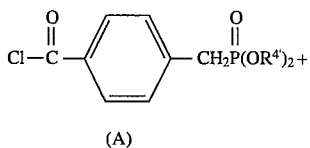

(A)

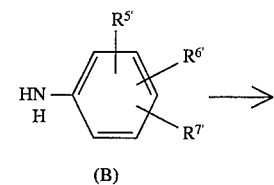

(B)

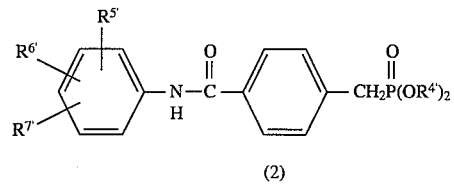

(2)

wherein $R^{4'}$, $R^{5'}$, $R^{6'}$, and $R^{7'}$ are the same as defined above.

According to Reaction Scheme-1, a compound of general formula (2) can be obtained by reacting a carboxylic acid chloride derivative (A) with an amine (B).

The above-mentioned reaction is carried out usually in an appropriate solvent in the presence of a de-acidifying agent. As to the de-acidifying agent, any known ones may be used so far as they exercise no adverse influence on the reaction. Preferable specific examples of the de-acidifying agent include tertiary amines such as triethylamine, diethylaniline, N-methylmorpholine, pyridine, 4-dimethylaminopyridine and the like. Examples of the solvent usable in this reaction include aromatic and aliphatic hydrocarbons such as benzene, toluene, xylene, petroleum ether and the like; acyclic and cyclic ethers such as diethyl ether, 1,2-dimethoxyethane, tetrahydrofuran (THF), 1,4-dioxane and the like; ketones such as acetone, methyl ethyl ketone, acetophenone and the like; halogenated hydrocarbons such as dichloromethane, chloroform, carbon tetrachloride, 1,2-dichloroethane and the like; etc.

In the above-mentioned reaction, the ratio of the carboxylic acid chloride derivative (A) to amine (B) is not particularly restricted. Generally, however, it is preferable to use the carboxylic acid chloride derivative (A) in an amount ranging from equimolar to excessive amount to the amine (B). The de-acidifying agent is preferably used in an amount ranging from equimolar to somewhat excessive to the carboxylic acid chloride derivative (A). The reaction can progress under any of cooled temperature condition, ambient temperature condition and heated temperature condition. Generally, it is preferable to adopt a temperature condition ranging from the neighborhood of ambient temperature to the reflux temperature. The reaction is generally completed in about 0.5 to 10 hours.

The objective compound obtained according to the method represented by Reaction Scheme-1 can be isolated from the reaction system by the conventional separating means and can be purified. As to the means for the isolation and purification, solvent extraction, distillation, recrystallization, column chromatography, preparative thin layer chromatography and the like can be adopted.

WORKING EXAMPLES

Figure 1:
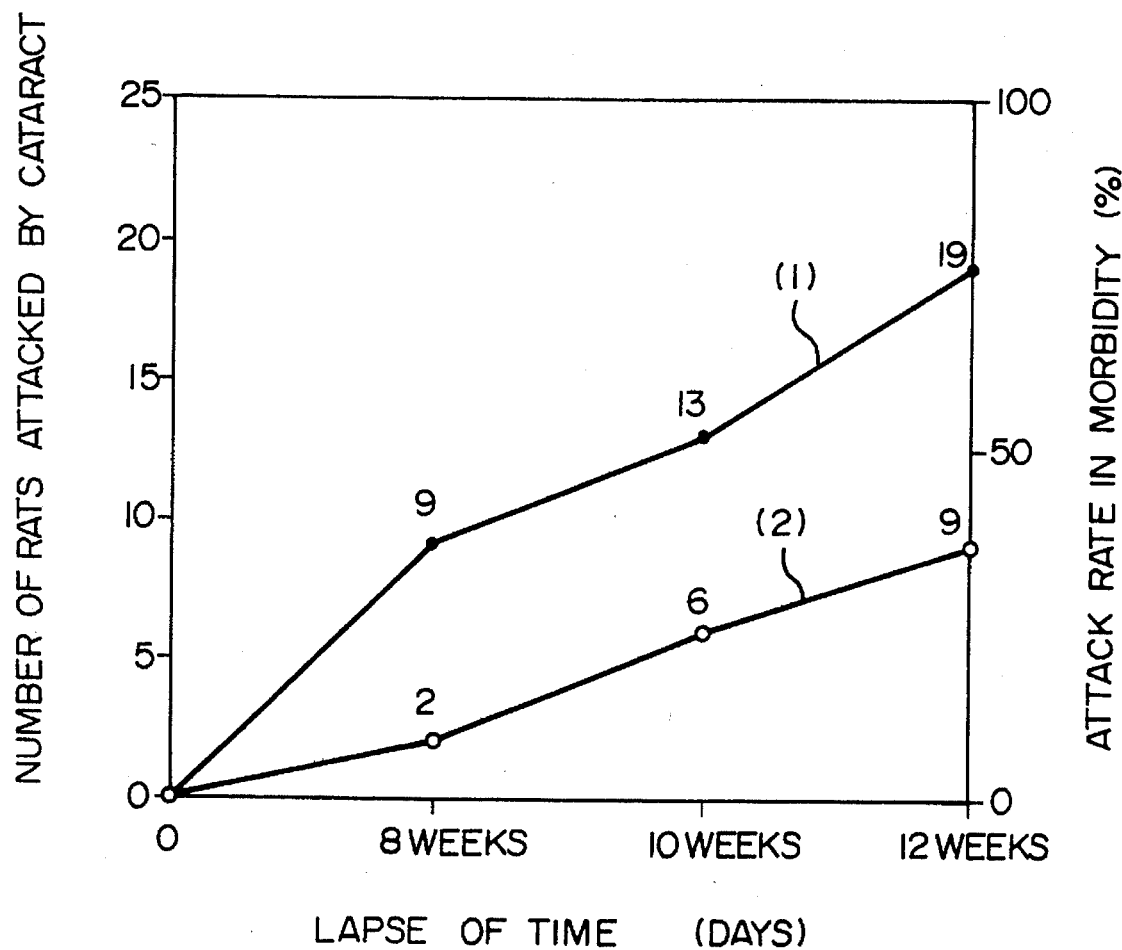
FIG. 1 is a graph illustrating the result of Pharmacological Test Example 1 to demonstrate the cataract-preventive effect of the agent for preventing and treating cataract of the present invention.

Next, production examples of the agent for preventing and treating cataract of the invention are presented below in order to explain the invention in more detail, and thereafter preparation examples illustrating the formulations of the invention are presented.

EXAMPLE 1

Preparation of 4-diethoxyphosphinoylmethyl-N-(4-bromo-2-cyanophenyl)benzamide

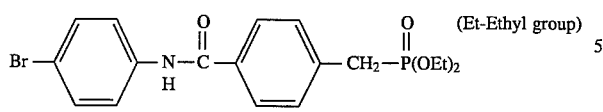

2-Amino-5-bromobenzonitrile (3.94 g, 20 millimoles), triethylamine (2.22 g, 22 millimoles) and 4-dimethylaminopyridine (0.49 g, 4 millimoles) were dissolved in 40 ml of dry dichloromethane, to which was slowly added dropwise a solution of 4-diethoxyphosphinoylmethylbenzoyl chloride (5.81 g, 20 millimoles) in 40 ml dry dichloromethane while cooling the system with ice and stirring it. After stirring the resulting mixture at ambient temperature for 10 hours, the reaction mixture was mixed with 50 ml of water and extracted with chloroform. The chloroform layer was dried on anhydrous sodium sulfate and the solvent was removed by evaporation under reduced pressure. Purification of the residue by a silica gel column chromato-graphy using 1:2 mixture of chloroform and ethyl acetate as an eluent, followed by recrystallization from benzene-n-hexane mixture, gave 2.94 g of 4-diethoxyphosphinoylmethyl-N-(4-bromo-2-cyanophenyl)benzamide as a colorless crystalline product melting at 165°–166° C. (after recrystallization from benzene-n-hexane).

EXAMPLES 2–7

By using appropriate starting compounds, the procedure of Example 1 was repeated to obtain the objective compounds shown in Table 1.

TABLE 1

| (Et = Ethyl group) |
| --- |

| Example 2 | |
| --- | --- |
| Structural formula: | 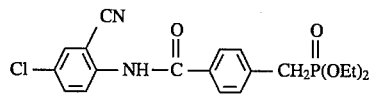 |
| Properties: | mp 171–172° C., after recrystallization from chloroform/n-hexane |
| Example 3 | |
| Structural formula: | 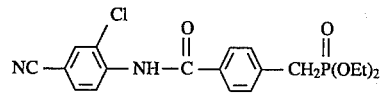 |
| Properties: | mp 152–154° C., after recrystallization from benzene/n-hexane |
| Example 4 | |
| Structural formula: | 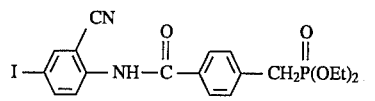 |
| Properties: | mp 176–177° C., after recrystallization from benzene |
| Example 5 | |
| Structural formula: | 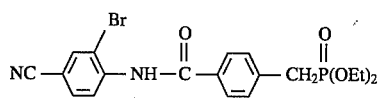 |
| Properties: | mp 152–154° C., after recrystallization from benzene/n-hexane |
| Example 6 | |
| Structrual formula: | 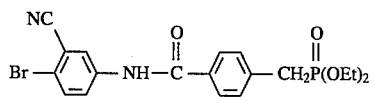 |
| Properties: | mp 208.5–209.5° C., after recrystallization from benzene/n-hexane |
| Example 7 | |
| Structural formula: | 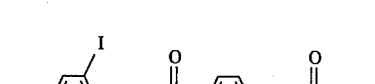 |
| Properties: | mp 163–165° C., after recrystallization from benzene/n-hexane |

Next, specific examples of pharmaceutical preparations of the present invention for preventing and treating cataract will be mentioned below.

PHARMACEUTICAL PREPARATION EXAMPLE 1

Preparation of Tablets

A tablet preparation (1,000 tablets) containing 250 mg of 4-diethoxyphosphinoylmethyl-N-(4-chlorophenyl)benzamide [hereinafter referred to as Compound (I)] per tablet as active ingredient was prepared according to the following formulation.

| Ingredients | Amount (g) |
| --- | --- |
| Compound (I) | 250 |
| Lactose (Japanese Pharmacopoeia grade) | 33.3 |
| Corn starch (Japanese Pharmacopoeia grade) | 16.4 |
| Carboxymethyl cellulose calcium (Japanese Pharmacopoeia grade) | 12.8 |
| Methyl cellulose (Japanese Pharmacopoeia grade) | 6.0 |
| Magnesium stearate (Japanese Pharmacopoeia grade) | 1.5 |
| Total | 320 |

According to the formulation mentioned above, Compound (I), lactose, corn starch and carboxymethyl cellulose calcium were thoroughly mixed together and granulated together with aqueous solution of methyl cellulose. The granules thus obtained were passed through a 24 mesh sieve, mixed with magnesium stearate, and pressed to form tablets.

PREPARATION EXAMPLE 2

Preparation of Capsules

A hard gelatin capsule preparation (1,000 capsules) containing 250 mg of 4-diethoxyphosphinoylmethyl-N-(4-bromo-2-cyanophenyl)benzamide [hereinafter referred to as Compound (II)] per capsule as active ingredient was prepared according to the following formulation.

| Ingredients | Amount (g) |
| --- | --- |
| Compound (II) | 250 |
| Crystalline cellulose (Japanese Pharmacopoeia grade) | 30 |
| Corn starch (Japanese Pharmacopoeia grade) | 17 |
| Talc (Japanese Pharmacopoeia grade) | 2 |
| Magnesium stearate (Japanese Pharmacopoeia grade) | 1 |
| Total | 300 |

According to the formulation mentioned above, the ingredients having previously been powdered finely were thoroughly mixed together so as to give a uniform mixture, and the mixture thus obtained was filled into a gelatin capsule for oral use of desired dimensions to obtain the objective capsule.

PREPARATION EXAMPLE 3

Preparation of Granules

A granular preparation (1,000 g) containing 500 mg of 4-diethoxyphosphinoylmethyl-N-phenylbenzamide [hereinafter referred to as Compound (III)] per gram as active ingredient was prepared according to the following recipe.

| Ingredients | Amount (g) |
| --- | --- |
| Compound (III) | 500 |
| Corn starch (Japanese Pharmacopoeia grade) | 250 |
| Lactose (Japanese Pharmacopoeia grade) | 100 |
| Crystalline cellulose (Japanese Pharmacopoeia grade) | 100 |
| Carboxymethyl cellulose calcium (Japanese Pharmacopoeia grade) | 40 |
| Hydroxypropyl cellulose (Japanese Pharmacopoeia grade) | 10 |
| Total | 1,000 |

According to the formulation mentioned above, Compound (III), corn starch, lactose, crystalline cellulose and carboxymethyl cellulose calcium were mixed together. The mixture thus obtained was kneaded together with aqueous solution of hydroxypropyl cellulose, granulated with extrusion-granulator and dried at 50° C. for 2 hours to obtain the objective granular preparation.

Next, examples of pharmacological tests on the active ingredient compound in the pharmaceutical composition of the invention are mentioned below.

PHARMACOLOGICAL TEST-1

Streptozotocin (65 mg/kg) was intravenously injected to Wistar strain rat (male, 6-week old, 25 rats in one group) to prepare rat models of diabetes mellitus. From 5 days after the administration, the rats having diabetes mellitus were raised as control group while freely giving them a cholesterol-containing feed containing 0.25% of cholesterol, 0.40% of sodium cholate and 2.50% of olive oil. To the test group, the same cholesterol-containing feed as above was freely given and, at the same time, 30 mg/kg/day of the compound of Example 1 was orally given as a test compound, over a period of 12 weeks.

FIG. 1 illustrates the results thus obtained.

In FIG. 1, the ordinate signifies the number of rats attacked by cataract (heads) and the attack rate in morbidity (%); the while abscissa does the lapse of time (weeks) counted by taking the fifth administration day of Streptozotocin as standard (zero time). In FIG. 1, (1) expresses control group to which no test compound was administered, while (2) expresses test group to which the test compound was administered.

It is apparent from FIG. 1 that the test group to which the carboxylic acid amide derivative of the invention, namely the active ingredient compound of the agent for preventing and treating cataract of the present invention, was administered is markedly suppressed in the attack rate in morbidity as compared with the control group to which the agent was not administered. This result demonstrates that the agent of the invention exhibits an excellent effect on the prevention and treatment of cataract.

PHARMACOLOGICAL TEST-2

The procedure of Pharmacological Test-1 was repeated, except that the following compounds shown in Table 2 were used as the test compounds.

TABLE 2

Text compound A:

4-Diethoxyphosphinylmethyl-N-phenylbenzamide

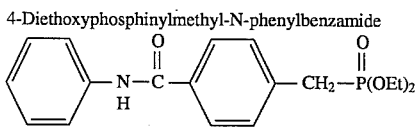

Text compound B:

4-Diethoxyphosphinylmethyl-N-(4-chlorophenyl)benzamide

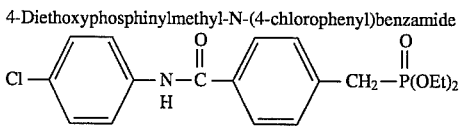

Text compound C:

4-Diethoxyphosphinylmethyl-N-benzyl-N-(3,4-dichlorophenyl)benzamide

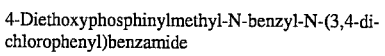

Text compound D:

4-Diethoxyphosphinylmethyl-N-(4-trifluoromethylphenyl)benzamide

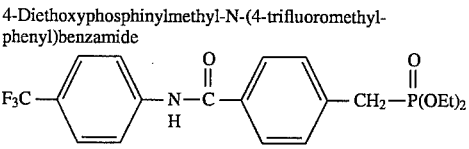

Eight weeks after, the number of rats attacked by cataract was counted. Table 3 illustrates the results, wherein the denominator is the number of rats used in the test. Table 3 also illustrates the results given by the control group to which no test compound was administered.

TABLE 3

| Test compound | Number of rats attacked by cataract (heads) |
| --- | --- |
| A | 5/25 |
| B | 5/25 |
| C | 5/25 |
| D | 3/25 |
| None (control) | 10/25 |

It is apparent from Table 3 that the test groups to which each test compounds (carboxylic acid amide derivative) was administered were all suppressed in the attack rate in morbidity of cataract. This result demonstrates that the therapeutic agents of the present invention exhibit an excellent effect in the prevention and treatment of cataract.

What is claimed is:

1. A method of treating cataract comprising administering, as an active ingredient, a therapeutically effective amount of a carboxylic acid amide derivative represented by the following general formula:

wherein:

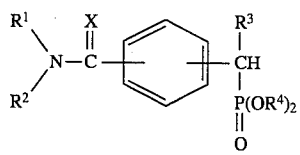

$R^1$ and $R^2$ taken individually each represents a hydrogen atom, an alkyl group, a cycloalkyl group, a diphenyl-lower alkyl group or a group of the formula:

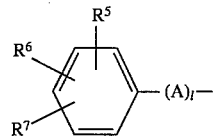

in which $R^5$, $R^6$ and $R^7$ each represents a hydrogen atom, a halogen atom, a nitro group, a lower alkoxy group, a lower alkoxycarbonyl group, a lower alkyl group, a halogen-substituted lower alkyl group, a cyano group, a carboxyl group or a hydroxyl group;

A represents a lower alkaline group and l represents 0 or 1;

$R^3$ represents a hydrogen atom, an alkyl group or a phenyl-lower alkyl group;

$R^4$ represents a lower alkyl group or a phenyl group; and

X represents an oxygen atom or a sulfur atom; to a patient in need of the same.

2. The method of treating cataract according to claim 1, wherein the active ingredient is selected from the group consisting of carboxylic acid amide derivatives represented by the general formula:

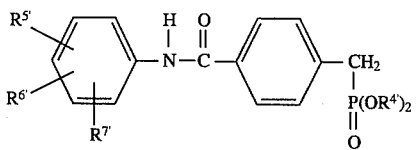

wherein $R^{4'}$ represents a lower alkyl group;

$R^{5'}$ represents a cyano group, $R^{6'}$ represents a halogen atom; and $R^{7'}$ represents a hydrogen atom or a halogen atom.

3. The method of treating cataract according to claim 2, wherein the active ingredient is selected from the group consisting of carboxylic acid amide derivatives represented by the general formula:

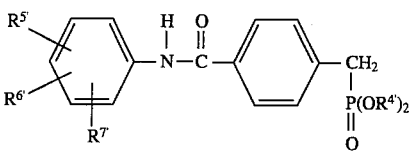

wherein
- $R^{4'}$ represents an ethyl group,
- $R^{5'}$ represents a cyano group,
- $R^{6'}$ represents a bromine atom; and
- $R^{7'}$ represents a hydrogen atom.

4. The method of treating cataract according to claim 3, wherein the active ingredient is 4-diethoxyphosphinoylmethyl-N-(4-bromo-2-cyanophenyl)-benzamide.

\* \* \* \* \*